US008691200B2

(12) United States Patent
Vilbert

(10) Patent No.: US 8,691,200 B2
(45) Date of Patent: Apr. 8, 2014

(54) PUMP-DISPENSER BOTTLE DEVICE CONTAINING A POLYCONDENSATE COMPRISING AT LEAST ONE POLYURETHANE AND/OR POLYUREA UNIT

(75) Inventor: Arnaud Vilbert, Villeneuve-la-Garenne (FR)

(73) Assignee: L'Oreal, Paris (FR)

( * ) Notice: Subject to any disclaimer, the term of this patent is extended or adjusted under 35 U.S.C. 154(b) by 660 days.

(21) Appl. No.: 12/633,236

(22) Filed: Dec. 8, 2009

(65) Prior Publication Data

US 2010/0086508 A1 Apr. 8, 2010

Related U.S. Application Data

(62) Division of application No. 09/582,714, filed as application No. PCT/FR99/02585 on Oct. 25, 1999, now abandoned.

(30) Foreign Application Priority Data

Nov. 3, 1998 (FR) ..................................... 98 13807

(51) Int. Cl.
*A61Q 5/12* (2006.01)
*A61Q 5/00* (2006.01)

(52) U.S. Cl.
USPC ...................... 424/70.12; 424/70.1

(58) Field of Classification Search
USPC .............................................. 424/70.12, 70.1
See application file for complete search history.

(56) References Cited

U.S. PATENT DOCUMENTS

| 5,458,871 | A | * | 10/1995 | Malawer et al. ................. 424/47 |
| 5,830,440 | A | * | 11/1998 | Sturla et al. ..................... 424/47 |
| 6,106,808 | A | * | 8/2000 | Bhatt et al. ...................... 424/45 |
| 6,395,265 | B1 | * | 5/2002 | Mougin et al. ............. 424/70.12 |

FOREIGN PATENT DOCUMENTS

| WO | WO 93/09757 | * | 5/1993 |
| WO | WO 97/25021 | * | 7/1997 |

* cited by examiner

*Primary Examiner* — Shengjun Wang
(74) *Attorney, Agent, or Firm* — The Marbury Law Group, PLLC

(57) ABSTRACT

The invention concerns aerosol devices comprising a reservoir containing, in a cosmetically suitable medium, a multiple-block polymer (A) comprising at least a polyurethane and/or polyurea unit and a film-forming polymer (B), the polymers (A) and (B) and the device being selected so as to obtain, at the device outlet, droplets of composition with average diameter less than 80 μm. The invention also concerns a hairstyling or hair-fixing method comprising the use of said devices and their use for making a hairstyling product.

10 Claims, No Drawings

PUMP-DISPENSER BOTTLE DEVICE CONTAINING A POLYCONDENSATE COMPRISING AT LEAST ONE POLYURETHANE AND/OR POLYUREA UNIT

This is a Divisional of application Ser. No. 09/582,714, filed Oct. 3, 2000 now abandoned, which is the national stage filing of International Application No. PCT/FR99/02585, filed Oct. 25, 1999. This application also claims benefit of priority of French Patent Application Nos. FR 98/13807, filed on Nov. 3, 1998, which is incorporated herein by reference.

The invention relates to pump-dispenser bottle devices comprising a reservoir which contains, in a cosmetically acceptable medium, a multiblock polymer (A) comprising at least one polyurethane and/or polyurea unit and a film-forming polymer (B), the polymers (A) and (B) and the device being chosen so as to obtain, on leaving the device, droplets of composition with an average diameter of less than 80 µm. The invention is also directed towards a process for shaping or holding the hairstyle comprising the use of these devices, and towards their use for the manufacture of a hair styling product.

Fixing of the hairstyle is an important element of styling which consists in maintaining the shape already given or in shaping the hair and fixing it simultaneously.

The hair products for shaping and/or maintaining the hairstyle which are the most common on the cosmetics market are spray compositions consisting essentially of a solution, usually an alcoholic and/or aqueous solution, and one or more materials, generally polymer resins, the function of which is to form welds between the hairs, these materials also being known as fixing materials, as a mixture with various cosmetic adjuvants. This solution can be packaged, for example, in a pump-dispenser bottle.

To satisfy the environmental protection obligations, compositions for fixing the hairstyle need to discharge fewer and fewer volatile organic compounds (VOCs). To this end, the amount of volatile organic solvents in the composition is reduced and these solvents are replaced with water. However, this change of the formulation of hair compositions has the harmful effect of greatly increasing their viscosity.

Packaging in pump-dispenser bottle form is especially practical for users who can easily measure out the amount of product which they wish to apply. However, this type of packaging occasionally makes it difficult to apply the product uniformly on the hair, since the droplets of product leaving the pump-dispenser bottle are often too large. This drawback is particularly pronounced for viscous compositions for which fine droplets are difficult to obtain.

The quality of the spraying obtained by means of a pump-dispenser bottle device, i.e. essentially the distribution of the droplets in space at the nozzle outlet, depends greatly on the chemical constitution of the composition used. Most particular advantage is thus given to the preparation of pump-dispenser bottle devices which give rise to fine droplets, despite a high viscosity of the compositions.

Patent DE 195 41 326 discloses the preparation of styling compositions comprising a polymer containing polyurethane units as fixing polymer. However, the devices can be improved in particular as regards the cosmetic properties which they give to the hair, while at the same time offering better spraying quality.

Against all expectation, the Applicant has discovered, surprisingly and unexpectedly, that it is possible to prepare pump-dispenser bottle devices which satisfy the requirements expressed above, by carrying out a selection, on the one hand, on the cosmetic composition, and, on the other hand, on the means for distributing this composition.

A subject of the invention is a pump-dispenser bottle device comprising a reservoir containing a hair composition, as well as means for distributing the composition, characterized in that:
(1) the composition comprises, in a cosmetically acceptable medium, at least one polycondensate (A) comprising at least one polyurethane and/or polyurea block and at least one film-forming polymer (B) which is different from (A);
(2) the polymers (A) and (B) and the device being chosen so as to obtain, on leaving the device, droplets of composition with an average diameter of less than or equal to 80 µm.

Another subject of the invention relates to a process for shaping or holding the hairstyle comprising the use of this pump-dispenser bottle device.

Yet another subject of the invention relates to the use of this device for the manufacture of a hair styling product.

The polycondensates comprising at least one polyurethane and/or polyurea block which are particularly targeted by the present invention are those described in the patents EP 0,751,162, EP 0,637,600, FR 2,743,297 and EP 0,648,485 of which the Applicant is the proprietor, as well as the patents EP 0,656,021 or WO 94/03510 from the company BASF and EP 0,619,111 from the company National Starch.

The polycondensates used in accordance with the invention can be soluble in the cosmetically acceptable medium, in particular after neutralization with an organic or inorganic base, or alternatively can form a dispersion in this medium. In this case, the dispersion can comprise at least 0.05% of surfactant which allows the polycondensate to form a dispersion and to be maintained in dispersion.

According to the invention, any type of surfactant can be used in the said dispersion, but preferably a nonionic surfactant. The average size of the polycondensate particles in the dispersion is preferably between 0.1 and 1 micron.

By way of example, the polycondensate can be formed by an arrangement of blocks, this arrangement being obtained in particular from:
(1) at least one compound which contains two or more than two active hydrogen atoms per molecule;
(2) at least one diol or a mixture of diols containing acid radicals or their salts;
(3) at least one di- or polyisocyanate.

Advantageously, the compounds (1) are chosen from the group comprising diols, diamines, polyesterols and polyetherols, or a mixture thereof.

The compounds (1) which are preferred are the linear polyethylene and polypropylene glycols, in particular those which are obtained by a reaction of ethylene oxide or propylene oxide with water or diethylene or dipropylene glycol in the presence of sodium hydroxide as catalyst. These polyglycols generally have a molecular weight of between about 600 and 20,000.

Other preferred organic compounds are those which have mercapto, amino, carboxyl or hydroxyl groups. Among these, mention may be made more particularly of polyhydroxy compounds such as polyether diols, polyester diols, polyacetal diols, polyamide diols, polyesterpolyamide diols, poly(alkylene ether) diols, polythioether diols and polycarbonate diols.

The preferred polyether diols are, for example, the condensation products of ethylene oxide, of propylene oxide or of tetrahydrofuran, their copolymerization or condensation products, which may be grafted or blocks, such as mixtures of condensates of ethylene oxide and propylene oxide, and the products of polymerization of olefins, at high pressure, with alkylene oxide condensates. Suitable polyethers are prepared, for example, by condensation of alkylene oxides and polyhydric alcohols, such as ethylene glycol, 1,2-propylene glycol and 1,4-butanediol.

The polyester diols, polyesteramides and polyamide diols are preferably saturated and are obtained, for example, from the reaction of saturated or unsaturated polycarboxylic acids with polyhydric alcohols, diamines or polyamines. Adipic acid, succinic acid, phthalic acid, terephthalic acid and maleic acid can be used, for example, to prepare these compounds. Polyhydric alcohols that are suitable for preparing the polyesters include, for example, ethylene glycol, 1,2-propylene glycol, 1,4-butanediol, neopentyl glycol and hexanediol. Amino alcohols, for example ethanolamine, can also be used. Diamines that are suitable for preparing the polyesteramides are ethylenediamine and hexamethylenediamine.

Suitable polyacetals can be prepared, for example, from 1,4-butanediol or from hexanediol and from formaldehyde. Suitable polythioethers can be prepared, for example, by condensation reaction between thioglycols, either alone or in combination with other glycols such as ethylene glycol, 1,2-propylene glycol or with other polyhydroxylated compounds. Polyhydroxylated compounds already containing urea or urethane groups, natural polyols, which can be further modified, for example castor oil and carbohydrates, can also be used.

More preferably, the compound of group (1) is a polyesterol, in particular a polyester diol formed by the reaction of at least one (di)polyol ($1_a$) and at least one acid ($1_b$). The (di)polyol ($1_a$) is chosen in particular from the group comprising neopentyl glycol, 1,4-butanediol, hexanediol, ethylene glycol, diethylene glycol, propylene glycol, butylene glycol, neopentyl glycol and (di)polyethylene glycol. The acid ($1_b$) is chosen in particular from the group comprising phthalic acid, isophthalic acid, adipic acid and (poly)lactic acid.

A hydroxycarboxylic acid such as dimethylolpropanoic acid (DMPA) or a 2,2-hydroxymethylcarboxylic acid can be used in particular as compound (2). In general, the compound (2) is useful as a coupling block. The preferred compounds (2) are those comprising at least one poly(($\alpha$-hydroxydiolcarboxylic) acid).

The compounds (2) which are particularly preferred in accordance with the invention are those chosen from the group comprising 2,2-di(hydroxymethyl)acetic acid, 2,2-dihydroxymethylpropionic acid, 2,2-dihydroxymethylbutyric acid and 2,2-dihydroxymethylpentanoic acid.

The di- or polyisocyanate (3) can be chosen in particular from the group comprising hexamethylene diisocyanate, isophorone diisocyanate (IPDI), toluoylene diisocyanate, diphenylmethane 4,4'-diisocyanate (DPMD) and dicyclohexylmethane 4,4'-diisocyanate (DCMD), methylenebis(p-phenyl)diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate and 1,4-cyclohexane diisocyanate.

The polycondensate can be formed using an additional compound (4) which generally serves to extend the polycondensate chain. These compounds (4) can be chosen from the group comprising, in particular, saturated or unsaturated glycols such as ethylene glycol, diethylene glycol, neopentyl glycol or triethylene glycol, amino alcohols such as ethanolamine, propanolamine or butanolamine, heterocyclic, aromatic, cycloaliphatic and aliphatic primary amines, diamines, carboxylic acids such as aliphatic, aromatic or heterocyclic carboxylic acids, for instance oxalic acid, succinic acid, glutaric acid, adipic acid, sebacic acid or terephthalic acid, and aminocarboxylic acids. The preferred compounds (4) are aliphatic diols.

The polycondensates in accordance with the invention can also be formed from additional compounds (5) having a silicone skeleton, such as polysiloxanes, polyalkylsiloxanes or polyarylsiloxanes, in particular polyethylsiloxanes, polymethylsiloxanes and polyphenylsiloxanes, optionally containing hydrocarbon-based chains grafted onto the silicon atoms.

The polyurethane and/or polyurea blocks of the polymer used advantageously have a repeating base unit corresponding to the general formula below:

—X'—B—X'—CO—NH—R—NH—CO—   (I')

in which:

X' represents O and/or NH,

B is a divalent hydrocarbon-based radical, this radical being substituted or unsubstituted, and R is a divalent radical chosen from alkylene radicals of aromatic type, $C_1$ to $C_{20}$ aliphatic radicals or $C_1$ to $C_{20}$ cycloaliphatic radicals, these radicals being substituted or unsubstituted.

Preferably, the radical B is a $C_1$ to $C_{30}$ radical and bears a group containing one or more carboxylic functions and/or one or more sulphonic functions, the said carboxylic and/or sulphonic functions being in free form or else partially or totally neutralized with an inorganic or organic base.

The radical R is advantageously chosen from the radicals corresponding to the following formulae:

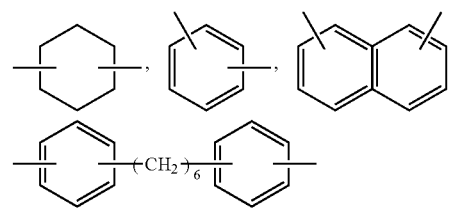

in which b is an integer between 0 and 3 and c is an integer between 1 and 20, preferably between 2 and 12.

In particular, the radical R is chosen from hexamethylene, 4,4'-biphenylenemethane, 2,4- and/or 2,6-tolylene, 1,5-naphthylene, p-phenylene and methylene-4,4-bis-cyclohexyl radicals and the divalent radical derived from isophorone.

The polycondensate used in accordance with the invention comprising at least one polyurethane and/or polyurea block can advantageously also comprise at least one polysiloxane block in which the repeating base unit corresponds, for example, to the general formula (II') below:

—X'—P—X'—CO—NH—R—NH—O—   (II')

in which:

P is a polysiloxane segment,

X' represents O and/or NH, and

R is a divalent radical chosen from alkylene radicals of aromatic type, $C_1$ to $C_{20}$ aliphatic radicals and $C_1$ to $C_{20}$ cycloaliphatic radicals, these radicals being substituted or unsubstituted.

Advantageously, the polysiloxane segment P corresponds to the general formula below:

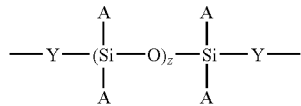
(III)

in which:

the radicals A, which can be identical or different, are chosen from, on the one hand, $C_1$ to $C_{20}$ monovalent hydrocarbon-based radicals which are free or substantially free of ethylenic unsaturation and, on the other hand, aromatic radicals, Y represents a divalent hydrocarbon-based radical, and z represents an integer chosen such that the average molecular weight of the polysiloxane segment is between 300 and 10,000.

In general, the divalent radical Y is chosen from alkylene radicals of formula —$(CH_2)_a$—, in which a represents an integer which can be between 1 and 10.

The radicals A can be chosen from alkyl radicals, in particular methyl, ethyl, propyl, isopropyl, butyl, pentyl, hexyl, octyl, decyl, dodecyl and octadecyl radicals, cycloalkyl radicals, in particular the cyclohexyl radical, aryl radicals, in particular phenyl and naphthyl, arylalkyl radicals, in particular benzyl and phenylethyl, and tolyl and xylyl radicals.

The cationic, anionic, amphoteric and nonionic film-forming polymers (B) which can be used in accordance with the invention are described below.

The cationic film-forming polymers which can be used according to the present invention are preferably chosen from polymers containing primary, secondary, tertiary and/or quaternary amine groups forming part of the polymer chain or directly attached thereto, and having a molecular weight of between 500 and about 5,000,000 and preferably between 1000 and 3,000,000.

Among these polymers, mention may be made more particularly of the following cationic polymers:

(1) homopolymers or copolymers derived from acrylic or methacrylic esters or amides and containing at least one of the units of the following formulae:

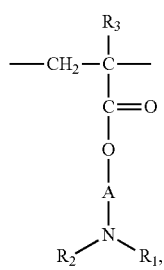
(A)

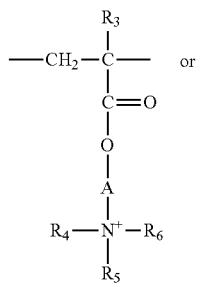
(B)

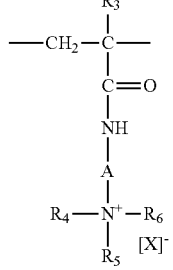
(C)

in which:
$R_3$ denotes a hydrogen atom or a $CH_3$ radical;
A is a linear or branched alkyl group of 1 to 6 carbon atoms or a hydroxyalkyl group of 1 to 4 carbon atoms;
$R_4$, $R_5$ and $R_6$, which may be identical or different, represent an alkyl group having from 1 to 18 carbon atoms or a benzyl radical;
$R_1$ and $R_2$ represent hydrogen or an alkyl group having from 1 to 6 carbon atoms;
X denotes a methosulphate anion or a halide such as chloride or bromide.

The copolymers of the family (1) also contain one or more units derived from comonomers which can be chosen from the family of acrylamides, methacrylamides, diacetone acrylamides, acrylamides and methacrylamides substituted on the nitrogen with lower alkyls, acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulphate or with a dimethyl halide, such as the one sold under the name Hercofloc by the company Hercules, copolymers of acrylamide and of methacryloyloxyethyltrimethylammonium chloride, described, for example, in patent application EP-A-080,976 and sold under the name Bina Quat P 100 by the company Ciba Geigy, the copolymer of acrylamide and of methacryloyloxyethyltrimethylammonium methosulphate, sold under the name Reten by the company Hercules, vinylpyrrolidone/dialkylaminoalkyl acrylate or methacrylate copolymers which are or are not quaternized, such as the products sold under the name "Gafquat" by the company ISP, such as, for example, "Gafquat 734" or "Gafquat 755" or alternatively the products known as "Copolymer 845, 958 and 937". These polymers are described in detail in French patents 2,077,143 and 2,393,573, dimethylaminoethyl methacrylate/vinylcaprolactam/vinylpyrrolidone terpolymers, such as the product sold under the name Gaffix VC 713 by the company ISP, and the quaternized vinylpyrrolidone/dimethylaminopropylmethacrylamide copolymer, such as the product sold under the name "Gafquat HS 100" by the company ISP;

(2) the quaternized polysaccharides described more particularly in U.S. Pat. Nos. 3,589,578 and 4,031,307, such as guar gums containing cationic trialkylammonium groups.

Such products are sold in particular under the trade names Jaguar C 13 S, Jaguar C 15 and Jaguar C 17 by the company Meyhall.

(3) quaternized copolymers of vinylpyrrolidone and of vinylimidazole, such as the products sold by BASF under the name Luviquat TFC;

(4) chitosans or salts thereof;
the salts which can be used are, in particular, chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer PC by the company Amerchol.

(5) Cationic cellulose derivatives, such as cellulose copolymers or cellulose derivatives grafted with a water-soluble monomer comprising a quaternary ammonium, which are described in particular in U.S. Pat. No. 4,131,576, such as hydroxyalkyl celluloses, for instance hydroxymethyl, hydroxyethyl or hydroxypropyl cellulose grafted in particular with a methacryloyloxyethyltrimethylammonium, methacrylamidopropyltrimethylammonium or dimethyldiallylammonium salt.

The commercial products corresponding to this definition are, more particularly, the products sold under the names ACelquat L 200" and ACelquat H 100" by the company National Starch.

The anionic film-forming polymers generally used are polymers containing groups derived from carboxylic acid, sulphonic acid or phosphoric acid and have a weight-average molecular weight of approximately between 500 and 5,000,000.

1) The carboxylic groups are provided by unsaturated mono- or dicarboxylic acid monomers such as those corresponding to the formula:

(II)

in which n is an integer from 0 to 10, $A_1$ denotes a methylene group, optionally connected to the carbon atom of the unsaturated group, or to the neighbouring methylene group when n is greater than 1, via a hetero atom such as oxygen or sulphur, $R_7$ denotes a hydrogen atom or a phenyl or benzyl group, $R_8$ denotes a hydrogen atom or a lower alkyl or carboxyl group, $R_9$ denotes a hydrogen atom, a lower alkyl group or a —$CH_2$—COOH, phenyl or benzyl group;

In the abovementioned formula, a lower alkyl radical preferably denotes a group having 1 to 4 carbon atoms and in particular methyl and ethyl.

The anionic film-forming polymers containing carboxylic groups which are preferred according to the invention are:
A) acrylic or methacrylic acid homo- or copolymers, or salts thereof and in particular the products sold under the names Versicol E or K by the company Allied Colloid and Ultrahold by the company BASF. The copolymers of acrylic acid and of acrylamide sold in the form of their sodium salt under the names Reten 421, 423 or 425 by the company Hercules, the sodium salts of polyhydroxycarboxylic acids.

B) copolymers of acrylic or methacrylic acids with a monoethylenic monomer such as ethylene, styrene, vinyl esters, acrylic or methacrylic acid esters, optionally grafted onto a polyalkylene glycol such as polyethylene glycol and optionally crosslinked. Such polymers are described in particular in French patent 1,222,944 and German patent application 2,330,956, the copolymers of this type containing an optionally N-alkylated and/or hydroxyalkylated acrylamide unit in their chain as described in particular in Luxembourg patent applications 75370 and 75371 or sold under the name Quadramer by the company American Cyanamid. Mention may also be made of copolymers of acrylic acid and of $C_1$-$C_4$ alkyl methacrylate and terpolymers of vinylpyrrolidone, of acrylic acid and of methacrylate of $C_1$-$C_{20}$ alkyl, for example lauryl such as the product sold by the company ISP under the name Acrylidone LM and methacrylic acid/ethyl acrylate/tert-butyl acrylate terpolymers such as the product sold under the name Luvimer 100 P by the company BASF.

C) copolymers derived from crotonic acid such as those containing vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Such polymers are described, inter alia, in French patents 1,222,944, 1,580,545, 2,265,782, 2,265,781, 1,564,110 and 2,439,798. Commercial products falling into this class are the resins 28-29-30, 26-13-14 and 28-13-10 sold by the company National Starch.

D) copolymers derived from $C_4$-$C_8$ monounsaturated carboxylic acids or anhydrides chosen from:
copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and esters thereof, the anhydride functions of these copolymers optionally being monoesterified or monoamidated. Such polymers are described in particular in U.S. Pat. Nos. 2,047,398, 2,723,248 and 2,102,113 and GB patent 839,805 and in particular those sold under the names Gantrez AN or ES by the company ISP.

copolymers comprising (i) one or more maleic, citraconic or itaconic anhydrides and (ii) one or more monomers chosen from allylic or methallylic esters optionally containing one or more acrylamide, methacrylamide, α-olefin, acrylic or methacrylic ester, acrylic or methacrylic acid or vinylpyrrolidone groups in their chain,
the anhydride functions of these copolymers optionally being monoesterified or monoamidated.

These polymers are described, for example, in French patents 2,350,384 and 2,357,241 by the Applicant.
E) polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be chosen in particular from:
polyvinylsulphonic acid salts having a weight-average molecular weight of approximately between 1000 and 100,000, as well as the copolymers with an unsaturated comonomer such as acrylic or methacrylic acids and their esters, as well as acrylamide or its derivatives, vinyl ethers and vinylpyrrolidone;
polystyrenesulphonic acid salts, the sodium salts having a weight-average molecular weight of about 500,000 and about 100,000, which are sold respectively under the names Flexan 500 and Flexan 130 by National Starch. These compounds are described in patent FR 2,198,719;

polyacrylamidesulphonic acid salts, those mentioned in U.S. Pat. No. 4,128,631 and more particularly polyacrylamidoethylpropanesulphonic acid sold under the name Cosmedia Polymer HSP 1180 by Henkel.

According to the invention, the anionic film-forming polymers are preferably chosen from acrylic acid copolymers, such as the acrylic acid/ethyl acrylate/N-tert-butylacrylamide terpolymer sold under the name Ultrahold Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymer sold under the name Gantrez ES 425 by the company ISP, the copolymers of methacrylic acid and methyl methacrylate sold under the name Eudragit L by the company Rohm Pharma, the copolymer of methacrylic acid and ethyl acrylate sold under the name Luvimer MAEX or MAE by the company BASF and the vinyl acetate/crotonic acid copolymer sold under the name Luviset CA 66 by the company BASF and the vinyl acetate/crotonic acid copolymer grafted with polyethylene glycol under the name Aristoflex A by the company BASF.

The anionic film-forming polymers which are most particularly preferred are chosen from the methyl vinyl ether/monoesterified maleic anhydride copolymer sold under the name Gantrez ES 425 by the company ISP, the acrylic acid/ethyl acrylate/N-tert-butylacrylamide terpolymer sold under the name Ultrahold Strong by the company BASF, the copolymers of methacrylic acid and methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymer of methacrylic acid and ethyl acrylate sold under the name Luvimer MAEX or MAE by the company BASF and the vinylpyrrolidone/acrylic acid/lauryl methacrylate terpolymer sold under the name Acrylidone LM by the company ISP.

The amphoteric film-forming polymers which can be used in accordance with the invention can be chosen from polymers containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers;

B and C can also denote a cationic polymer chain containing primary, secondary, tertiary or quaternary amine groups, in which at least one of the amine groups bears a carboxylic or sulphonic group connected via a hydrocarbon radical or alternatively B and C form part of a chain of a polymer containing an α,β-dicarboxylic ethylene unit in which one of the carboxylic groups has been made to react with a polyamine containing one or more primary or secondary amine groups.

The amphoteric film-forming polymers corresponding to the definition given above which are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537.

(2) polymers containing units derived from:

a) at least one monomer chosen from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.

(3) crosslinked and alkylated polyamino amides partially or totally derived from polyamino amides of general formula:

(III)

in which $R_{10}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the said acids to a bis(primary) or bis(secondary) amine, and Z denotes a bis (primary), mono- or bis(secondary) polyalkylene-polyamine radical and preferably represents:

(IV)

a) in proportions of from 60 to 100 mol %, the radical where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (IV) above in which x=2 and p=1 and which is derived from ethylenediamine, or the radical derived from piperazine:

c) in proportions of from 0 to 20 mol %, the —NH—$(CH_2)_6$—NH— radical derived from hexamethylenediamine, these polyaminoamines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) polymers containing zwitterionic units of formula:

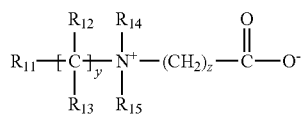

(V)

in which $R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom, methyl, ethyl or propyl, $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate:

By way of example, mention may be made of the copolymer of methyl methacrylate/dimethyl carboxymethylammonio methyl ethylmethacrylate such as the product sold under the name Diaformer 2301 by the company Sandoz.

(5) polymers derived from chitosan containing monomer units corresponding to the following formulae:

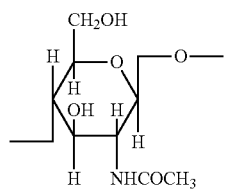

(D)

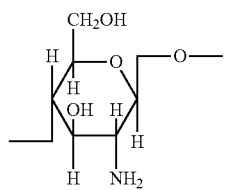

(E)

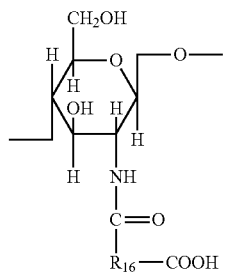

(F)

the unit D being present in proportions of between 0 and 30%, the unit E in proportions of between 5 and 50% and the unit F in proportions of between 30 and 90%, it being understood that, in this unit F, $R_{16}$ represents a radical of formula:

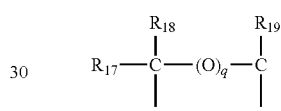

in which, if q=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being, in this case, a hydrogen atom; or, if q=1, $R_{17}$, $R_{18}$ and $R_{19}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (VI) are described, for example, in French patent 1,400,366:

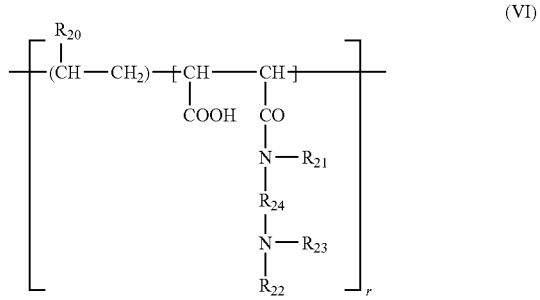

(VI)

in which $R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: —$R_{24}$—$N(R_{22})_2$, $R_{24}$ representing a —$CH_2$—$CH_2$—, —$CH_2$—$CH_2$—$CH_2$— or —$CH_2$—$CH$ ($CH_3$)— group, $R_{22}$ having the meanings mentioned above, as well as the higher homologues of these radicals and containing up to 6 carbon atoms.

(8) Amphoteric polymers of the type -D-X-D-X chosen from:

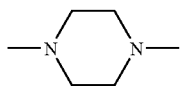

a) polymers obtained by the action of chloroacetic acid or sodium chloroacetate on compounds containing at least one unit of formula:

-D-X-D-X-D- (VII)

where D denotes a radical

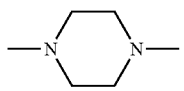

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) Polymers of formula:

-D-X-D-X (VII')

in which D denotes a radical
and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$-$C_5$)alkyl vinyl ether/maleic anhydride copolymers, the maleic anhydride being partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric film-forming polymers which are particularly preferred according to the invention are those of family (3), such as the copolymers whose CTFA name is octylacrylamide/acrylates/butylaminoethyl methacrylate copolymer, such as the products sold under the names Amphomer, Amhomer LV 71 or Lovocryl 47 by the company National Starch and those of family (4) such as the copolymer of methyl methacrylate/dimethyl carboxymethylammonio methyl ethylmethacrylate, sold, for example, under the name Diaformer Z301 by the company Sandoz.

The nonionic film-forming polymers which can be used according to the present invention are chosen, for example, from:

vinylpyrrolidone homopolymers;

copolymers of vinylpyrrolidone and vinyl acetate;

polyalkyloxazolines such as the polyethyloxazolines sold by the company Dow Chemical under the names Peox 50,000, Peox 200,000 and Peox 500,000;

vinyl acetate homopolymers, such as the product sold under the name Appretan EM by the company Hoechst, or the product sold under the name Rhodopas A 012 by the company Rhône-Poulenc;

copolymers of vinyl acetate and acrylic ester, such as the product sold under the name Rhodopas AD 310 by Rhône-Poulenc;

copolymers of vinyl acetate and ethylene, such as the product sold under the name Appretan TV by the company Hoechst;

copolymers of vinyl acetate and maleic ester, for example of dibutyl maleate, such as the product sold under the name Appretan MB Extra by the company Hoechst;

copolymers of polyethylene and maleic anhydride;

alkyl acrylate homopolymers and alkyl methacrylate homopolymers, such as the product sold under the name Micropearl RQ 750 by the company Matsumoto or the product sold under the name Luhydran A 848 S by the company BASF;

acrylic ester copolymers such as, for example, copolymers of alkyl acrylates and alkyl methacrylates, such as the products sold by the company Rohm & Haas under the names Primal AC-261 K and Eudragit NE 30 D, by the company BASF under the names Acronal 601, Luhydran LR 8833 or 8845, and by the company Hoechst under the names Appretan N 9213 or N 9212;

copolymers of acrylonitrile and a nonionic monomer chosen, for example, from butadiene and alkyl (meth)acrylates; mention may be made of the products sold under the names Nipol LX 531 B by the company Nippon Zeon or those sold under the name CJ 0601 B by the company Rohm & Haas;

polyurethanes, such as the products sold under the names Acrysol RM 1020 or Acrysol RM 2020 by the company Rohm & Haas, and the products Uraflex XP 401 UZ and Uraflex XP 402 UZ by the company DSM Resins;

copolymers of alkyl acrylate and urethane, such as the product 8538-33 by the company National Starch;

polyamides, such as the product Estapor LO 11 sold by the company Rhône-Poulenc;

unmodified or chemically modified nonionic guar gums.

The unmodified nonionic guar gums are, for example, the products sold under the name Vidogum GH 175 by the company Unipectine and under the name Jaguar C by the company Meyhall.

The modified nonionic guar gums which can be used according to the invention are preferably modified with $C_1$-$C_6$ hydroxyalkyl groups. Mention may be made, for example, of hydroxymethyl, hydroxyethyl, hydroxypropyl and hydroxybutyl groups.

These guar gums are well known in the state of the art and can be prepared, for example, by reacting corresponding alkene oxides, such as, for example, propylene oxides, with guar gum so as to obtain a guar gum modified with hydroxypropyl groups.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

The alkyl radicals of the nonionic polymers have from 1 to 6 carbon atoms except where otherwise mentioned.

According to the invention, it is also possible to use film-forming polymers of grafted silicone type comprising a polysiloxane portion and a portion consisting of a non-silicone organic chain, one of the two portions constituting the main polymer chain, the other being grafted onto the said main chain. These polymers are described, for example, in patent applications EP-A-0,412,704, EP-A-0,412,707, EP-A-0,640,105 and WO 95/00578, EP-A-0,582,152 and WO 93/23009 and U.S. Pat. Nos. 4,693,935, 4,728,571 and 4,972,037. These polymers are preferably anionic or nonionic.

Such polymers are, for example, copolymers which can be obtained by radical polymerization from the monomer mixture consisting of:
a) 50 to 90% by weight of tert-butyl acrylate;
b) 0 to 40% by weight of acrylic acid;
c) 5 to 40% by weight of silicone macromer of formula:

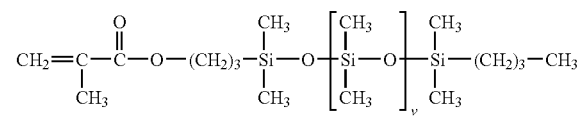

with v being a number from 5 to 700; the weight percentages being calculated relative to the total weight of the monomers.

Other examples of grafted silicone polymers are, in particular, polydimethylsiloxanes (PDMSs) onto which are grafted, via a thiopropylene-type connecting chain, mixed polymer units of the poly(meth)acrylic acid type and of the polyalkyl(meth)acrylate type and polydimethylsiloxanes (PDMSs) onto which are grafted, via a thiopropylene-type connecting chain, polymer units of the polyisobutyl(meth) acrylate type.

Film-forming polymers (B) which can also be used are functionalized or non-functionalized, silicone or non-silicone polyurethanes which are different from the polycondensates (A).

The distribution means, which forms a part of the pump-dispenser bottle device, generally consists of at least one pump functioning by suction and/or delivery of liquid and air. This pump is controlled by a distribution head which itself comprises a nozzle via which the composition is vaporized.

According to the invention, the pump-dispenser bottle device advantageously used is one which delivers an amount of composition of between 120 and 170 µl when the user presses once on the push-button, and preferably an amount of composition of between 140 and 160 µl.

In accordance with the invention, the droplet diameter is measured for a composition temperature in the region of 20° C. inside the pump-dispenser bottle device. In practice, the pump-dispenser bottle device is placed at room temperature and the droplet diameter is measured 20 cm from the nozzle.

The polycondensates used in accordance with the invention may be soluble in the cosmetically acceptable medium or may form a dispersion in this medium. In this case, the dispersion can comprise at least 0.05% of surfactant to allow the placing in dispersion and maintenance in dispersion of the polycondensate.

According to the invention, any type of surfactant can be used in the said dispersion, but preferably a nonionic surfactant. The average size of the polycondensate particles in the dispersion is preferably between 0.1 and 1 micron.

The composition in accordance with the invention advantageously comprises, as a relative proportion by weight relative to the total weight of the composition, between 0.1 and 30% of the polycondensate (A) comprising at least one polyurethane and/or polyurea block, more advantageously between 0.5 and 20% and even more advantageously between 1 and 10% of this polycondensate.

The composition in accordance with the invention advantageously comprises, as a relative proportion by weight relative to the total weight of the composition, between 0.1 and 30% of the film-forming polymer (B), more advantageously between 0.5 and 20% and even more advantageously between 1 and 10% of film-forming polymer (B).

It can comprise an additional organic solvent in a proportion ranging between 0.5 and 80%.

In accordance with the invention, the organic solvent is chosen in particular from the group comprising $C_1$ to $C_4$ alcohols such as ethanol or isopropanol, acetone, methyl ethyl ketone, methyl acetate, butyl acetate, ethyl acetate, dimethoxyethane, diethoxyethane and mixtures thereof. Ethanol is preferably used.

The compositions in accordance with the invention can moreover contain conventional cosmetic additives chosen in particular from fatty substances, thickeners, softeners, antifoaming agents, moisturizers, antiperspirants, basifying agents, dyes, pigments, fragrances, preserving agents, surfactants, polymers other than those of the invention, volatile or non-volatile silicones, in particular anionic silicones, polyols, proteins and vitamins.

A better understanding of the invention may be gained with the aid of the non-limiting example below.

EXAMPLE

The quality of the spraying obtained by means of pump-dispenser bottles in accordance with the invention is compared with that obtained with pump-dispenser bottles of the prior art.

The three pump-dispenser bottles in accordance with the invention all contain the same composition I comprising a polyurethane, and differ from each other in respect of the distribution means.

Composition I

| | |
|---|---|
| Lactic acid/ethylene glycol P (MIS - EG) - dimethylolpropanoic acid (DMPA) - isophorone diisocyanate polyester polycondensate | 6.6% |
| Polydimethyl/methylsiloxane containing propylthio-3-methylacrylate groups/meth-acrylate/methacrylic acid sold by 3M under the name VS80 | 0.1 g A.M. |
| Aminomethylpropanol | qs neutralization |
| Ethanol | 40% |
| Demineralized water | qs 100% |

A.M. means active material

The pump-dispenser bottles in accordance with the prior art contain polyurethane-free fixing compositions, namely Mighty Mist® sold by L=Oréal and Pantene® sold by Procter & Gamble.

The devices below are used to package the compositions:

Euromist 140 sold by Seaquist, which delivers 140 μl of composition for each press exerted by the user, Euromist 160 sold by Seaquist, which delivers 160 μl of composition for each press exerted by the user, Perfect PZ11/140 sold by Valois, which delivers 140 μl of composition for each press exerted by the user.

The average diameter of the droplets leaving the pump-dispenser bottles is determined, along with the minimum and maximum diameters. The results are collated in Table 1 below.

TABLE 1

|  | Average diameter (μm) | Minimum diameter (μm) | Maximum diameter (μm) |
| --- | --- | --- | --- |
| Composition I + Euromist 140 | 72 | 67 | 74 |
| Composition I + Euromist 160 | 74 | 72 | 76 |
| Composition I + Perfect PZ11/140 | 78 | 76 | 86 |
| Mighty Mist ® + Euromist 140 | 85 | 81 | 89 |
| Pantène ® + Euromist 160 | 89 | 85 | 92 |

It results therefrom that pump-dispenser bottles in accordance with the present invention give finer droplets than the pump-dispenser bottles according to the prior art. The pump-dispenser bottles in accordance with the invention thus produce a more homogeneous spraying of the product on the hair than the pump-dispenser bottles of the prior art.

The invention claimed is:

1. A process for shaping or holding a hairstyle, comprising: dispensing a hair composition using a dispenser device, said dispenser device comprising a reservoir containing said hair composition; wherein
   (i) the composition comprises, in a cosmetically acceptable medium, at least one polycondensate (A) comprising at least one block chosen from polyurethane and polyurea blocks and at least one film-forming polymer (B), wherein the at least one polycondensate (A) is different from the at least one film-forming polymer (B), and wherein the at least one polycondensate (A) is formed by an arrangement of blocks, said arrangement of blocks being obtained from:
   (1) at least one compound which contains at least two active hydrogen atoms per molecule;
   (2) at least one substance chosen from at least one diol containing at least one acid radical and the salts of said at least one diol; and
   (3) at least on isocyanate chosen from di- and polyisocyanates and
   wherein the at least one polycondensate (A) is formed from at least one compound having a silicone skeleton chosen from polysiloxanes, polyalkylsiloxanes and polyarylsiloxanes;
   and wherein the at least one polycondensate (A) is not hydrophilic;
   wherein the at least one film-forming polymer (B) is chosen from anionic polymers chosen from vinyl acetate/vinyl tert-butylbenzoate/crotonic acid terpolymers; and
   (ii) the at least one polycondensate (A), the at least one film-forming polymer (B), and the device being chosen so as to obtain droplets of said hair composition having an average diameter of less than or equal to 80 μm upon dispensing.

2. The process of claim 1, wherein the composition further comprises an organic solvent.

3. The process of claim 1, wherein the at least one substance chosen from at least one diol containing at least one acid radical and the salts of said at least one diol, is 2,2-hydroxymethylcarboxylic acid.

4. The process of claim 1, wherein the at least on isocyanate chosen from di- and polyisocyanates is chosen from hexamethylene diisocyanate, isophorone diisocyanate, toluoylene diisocyanate, diphenylmethane 4,4'-diisocyanate, dicyclohexylmethane 4,4'-disocyanate, methylenebis(p-phenyl)diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate and 1,4-cyclohexane diisocyanate.

5. The process of claim 1, wherein the at least one additional compound having a silicone skeleton comprises hydrocarbon-based chains grafted onto the silicone atoms.

6. The process of claim 1, wherein the composition comprises at least one polycondensate (A) in an amount ranging from 0.1 to 30%, relative to the total weight of the composition.

7. The process of claim 1, wherein the composition comprises at least one film-forming polymer (B) in an amount ranging from 0.1 to 30%, relative to the total weight of the composition.

8. The process of claim 1, wherein the composition further comprises at least one organic solvent in an amount ranging from 0.5 to 80%, relative to the total weight of the composition.

9. The process of claim 1, wherein said dispenser device comprises a push button, and wherein the composition is delivered in an amount ranging from 12 μl to 170 μl, when the user presses once on the push button.

10. The process of claim 1, wherein the composition further comprises at least one cosmetic additive chosen from fatty substances, thickeners, softeners, antifoaming agents, moisturizers, antiperspirants, basifying agents, dyes, pigments, fragrances, preserving agents, surfactants, and volatile or non-volatile silicones.

* * * * *

UNITED STATES PATENT AND TRADEMARK OFFICE
CERTIFICATE OF CORRECTION

PATENT NO. : 8,691,200 B2
APPLICATION NO. : 12/633236
DATED : April 8, 2014
INVENTOR(S) : Arnaud Vilbert Page 1 of 1

It is certified that error appears in the above-identified patent and that said Letters Patent is hereby corrected as shown below:

In the Claims

Claim 1, Col. 17, line 52, change "on" to -- one --.

Claim 5, Col. 18, lines 31-32, delete "additional".

Claim 9, Col. 18, line 48, change "12" to -- 120 --.

Signed and Sealed this
Fifteenth Day of July, 2014

Michelle K. Lee
*Deputy Director of the United States Patent and Trademark Office*